(12) United States Patent
Govyadinov et al.

(10) Patent No.: US 11,815,430 B2
(45) Date of Patent: Nov. 14, 2023

(54) NUCLEIC ACID DETECTION

(71) Applicant: Hewlett-Packard Development Company, L.P., Spring, TX (US)

(72) Inventors: Alexander Govyadinov, Corvallis, OR (US); Brett E. Dahlgren, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 17/059,732

(22) PCT Filed: Feb. 22, 2019

(86) PCT No.: PCT/US2019/019199
§ 371 (c)(1),
(2) Date: Nov. 30, 2020

(87) PCT Pub. No.: WO2020/171823
PCT Pub. Date: Aug. 27, 2020

(65) Prior Publication Data
US 2021/0372925 A1 Dec. 2, 2021

(51) Int. Cl.
*G01N 21/64* (2006.01)
*G01N 27/00* (2006.01)
*B01L 3/00* (2006.01)
*G01N 27/27* (2006.01)

(52) U.S. Cl.
CPC .... *G01N 21/6428* (2013.01); *B01L 3/502715* (2013.01); *G01N 21/645* (2013.01); *G01N 27/00* (2013.01); *G01N 27/27* (2013.01); *B01L 2300/0627* (2013.01)

(58) Field of Classification Search
None
See application file for complete search history.

(56) References Cited

U.S. PATENT DOCUMENTS

| 6,743,581 B1 | 6/2004 | Vo-Dinh |
| 9,194,859 B2 | 11/2015 | Emeric et al. |
| 2002/0123048 A1* | 9/2002 | Gau ............ B01L 3/5088 435/7.1 |
| 2004/0053290 A1* | 3/2004 | Terbrueggen .... G01N 35/00871 205/777.5 |
| 2004/0157263 A1 | 8/2004 | Diessel et al. |

(Continued)

FOREIGN PATENT DOCUMENTS

| EP | 3001182 | 3/2016 |
| JP | 2018141738 | 9/2018 |

(Continued)

*Primary Examiner* — Neil N Turk
(74) *Attorney, Agent, or Firm* — Foley & Lardner LLP

(57) ABSTRACT

A nucleic acid detection device includes a microfluidic opening and a sensor stack. The sensor stack includes an electrochemical electrode and a photodetector. The electrochemical electrode is formed of a conductive material that is transparent to a fluorescent emission, the electrochemical electrode including a first side and an opposite second side, wherein the first side is exposed to the microfluidic opening. The photodetector is positioned relative to the second side of the electrochemical electrode to optically receive the fluorescent emission when passed through the electrochemical electrode.

18 Claims, 6 Drawing Sheets

(56) References Cited

U.S. PATENT DOCUMENTS

| | | | |
|---|---|---|---|
| 2006/0098927 A1* | 5/2006 | Schmidt | G01N 21/645 385/129 |
| 2007/0227885 A1* | 10/2007 | Okada | G01N 27/3275 204/403.01 |
| 2009/0159442 A1 | 6/2009 | Collier et al. | |
| 2009/0205979 A1 | 8/2009 | Bekki et al. | |
| 2010/0282617 A1* | 11/2010 | Rothberg | G01N 27/4148 205/780.5 |
| 2011/0150705 A1 | 6/2011 | Doyle et al. | |
| 2011/0171749 A1 | 7/2011 | Alocilja et al. | |
| 2011/0312828 A1 | 12/2011 | Moini et al. | |
| 2011/0312841 A1* | 12/2011 | Silverbrook | C12Q 1/68 506/40 |
| 2012/0019828 A1* | 1/2012 | McCaffrey | G01N 21/645 439/55 |
| 2013/0008789 A1 | 1/2013 | Ronaghi et al. | |
| 2013/0143206 A1* | 6/2013 | McCaffrey | C12Q 1/6869 435/6.1 |
| 2014/0228247 A1 | 8/2014 | Flechsig et al. | |
| 2016/0025630 A1 | 1/2016 | Jensen et al. | |
| 2019/0137434 A1* | 5/2019 | Seker | G01N 27/3277 |

FOREIGN PATENT DOCUMENTS

| | | |
|---|---|---|
| WO | WO-2001083674 | 11/2001 |
| WO | WO-2013119719 | 8/2013 |
| WO | WO-2018136932 | 7/2018 |

* cited by examiner

NUCLEIC ACID DETECTION

BACKGROUND

Nucleic acid amplification and detection is a technique utilized in research, medical diagnostics, and forensic testing. The ability to amplify a small quantity of a sample of a nucleic acid to generate copies of the nucleic acid in the sample can permit research, medical diagnostic, and forensic tests that would not otherwise be permissible from the small quantity of the sample, for example.

DETAILED DESCRIPTION

Figure 1:
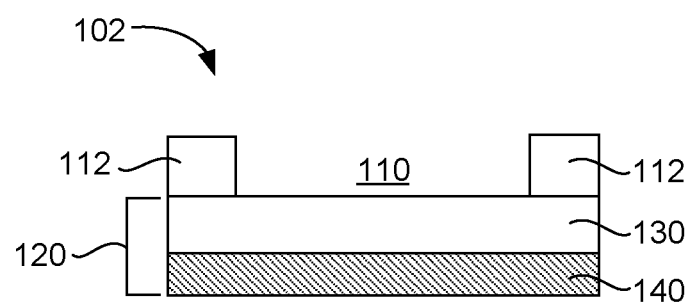
FIG. 1 graphically illustrates an example nucleic acid detection device in accordance with the present disclosure.

Nucleic acid amplification can include denaturing, annealing, and extending nucleic acid chains. During denaturing, an increased temperature can cause hydrogen bonds between bases in a double-stranded nucleic acid sample to break apart, resulting in two single strands realized from a formerly double-stranded nucleic acid. During annealing, the heated sample can then be cooled, enabling single stranded nucleic acid oligomers, such as primers, to attach to the complimentary nitrogen bases on the single strands of the nucleic acid. During extending of the nucleic acid chain, the temperature may be increased, for example, to enable a polymerase enzyme to extend the nucleic acid strand by adding nucleic acid bases. In real-time nucleic acid amplification, the amplification of a nucleic acid sample is monitored during the amplification. This can permit the quantification of nucleic acid concentration, gene expression, and sequencing.

In accordance with examples of the present disclosure, a nucleic acid detection device includes a microfluidic opening and a sensor stack. The sensor stack includes an electrochemical electrode and a photodetector. The electrochemical electrode is formed of a conductive material that is transparent to a fluorescent emission and includes a first side and an opposite second side. The first side is exposed to the microfluidic opening and the photodetector is positioned relative to the second side of the electrochemical electrode. The photodetector optically receives the fluorescent emission when passed through the electrochemical electrode. In one example, the conductive material includes a conductive metal oxide, a conductive polymer, or a conductive ceramic. In another example, the conductive material includes the conductive metal oxide and is selected from indium tin oxide, tin (IV) oxide, zinc tin oxide, bismuth-doped tin oxide, fluorine-doped tin oxide, or a combination thereof. In yet another example, the conductive material includes the conductive polymer and is selected from polypyrrole, oxidized derivative of polypyrrole, polythiophene, oxidized derivative of polythiophene, polyaniline, oxidized derivative of polyaniline, polyacetylene, oxidized derivative of polyacetylene, or a combination thereof. In a further example, the conductive material includes the conductive ceramic and is selected from bismuth strontium calcium copper oxide, yttrium barium copper oxide, thallium barium calcium copper oxide, mercury barium calcium copper oxide, fluorine doped lanthanide iron arsenic oxide, or a combination thereof. In one example, the photodetector includes a pin-photodiode, an avalanche photodiode, a phototransistor, a multi-junction photodiode, a charge coupling device, a complimentary metal-oxide semiconductor, a photo-sensor, a photo-resistor, a pyroelectric detector, a thermopile, or a combination thereof. In another example, the nucleic acid detection device is included in a lab-on-a-chip device. In yet another example, the nucleic acid detection device further includes an optically active dye filter having an average thickness from 1 µm to 100 µm located between the electrochemical electrode and the photodetector. In a further example, the nucleic acid detection device further includes an optically active dichroic filter having an average thickness from 0.5 µm to 100 µm located between the electrochemical electrode and the photodetector. In one example, the optically active dichroic filter includes from 5 to 250 individual layers, the individual layers having an average thickness ranging from 5 nm to 900 nm.

Also presented herein is a multiplex nucleic acid detection system. The multiplex nucleic acid detection system includes a nucleic acid device and a light source. The nucleic acid detection device includes a microfluidic opening and a sensor stack. The sensor stack includes an electrochemical electrode formed of a conductive material that is transparent to a fluorescent emission, the electrochemical electrode including a first side and an opposite second side, wherein the first side is exposed to the microfluidic opening, and a photodetector positioned at the second side of the electrochemical electrode to optically receive the fluorescent emission when passed through the electrochemical electrode. The light source is operable to emit an excitation electromagnetic energy onto the first side through the microfluidic opening. In one example, the system further includes a fluid with a fluorescing agent to interact with the excitation electromagnetic energy and emit a fluorescent emission, wherein the conductive material absorbs the excitation electromagnetic energy and is transparent to the fluorescent emission. In another example, the fluid is a nucleic acid amplifying solution can include a nucleic acid oligomer, a redox-active intercalating dye, or a combination thereof, and the fluorescing agent can include a fluorescent intercalating dye.

A method of nucleic acid detection is also disclosed herein. The method includes loading a nucleic acid amplifying fluid into a microfluidic opening of a nucleic acid detection device, wherein the nucleic acid amplifying fluid includes a nucleic acid oligomer, a redox-active intercalating dye, and a fluorescent intercalating dye. The method also include amplifying a nucleic acid within the nucleic acid detection device using the nucleic acid amplifying fluid, and emitting an excitation electromagnetic energy through the nucleic acid fluid and onto a first side of a sensor stack. The sensor stack includes an electrochemical electrode formed of a conductive material that is transparent to a fluorescent emission generated by interaction with the excitation electromagnetic energy. The sensor stack further including a photodetector positioned at the second side of the electrochemical electrode to optically receive the fluorescent emission when passed through the electrochemical electrode. The method also includes detecting double-stranded nucleic acids using the electrochemical electrode based on an electrochemical response generated by the redox-active intercalating dye, and detecting the fluorescent emission using the photodetector based on fluorescence generated by the florescent intercalating dye upon interaction with the electromagnetic energy. In one example, the method further includes simultaneously measuring a real time strength of an electrochemical response generated during amplification by the redox-active intercalating dye and fluorescent emissions generated during amplification by the fluorescent intercalating dye.

When discussing the nucleic acid detection device, the multiplex nucleic acid detection system, and the method of nucleic acid detection herein, these discussions can be considered applicable to one another whether or not they are explicitly discussed in the context of that example. Thus, for example, when discussing an electrochemical electrode with respect to a nucleic acid detection device, such disclosure is also relevant to and directly supported in the context of the multiplex nucleic acid detection systems and the method of multiplex nucleic acid detection.

Terms used herein will take on their ordinary meaning in the relevant technical field unless specified otherwise. In some instances, there are terms defined more specifically throughout the specification or included at the end of the present specification, and thus, these terms can have a meaning as described herein.

In accordance with examples of the present disclosure, a nucleic acid detection device 102 is shown in part in FIG. 1. The device can include a microfluidic opening 110 and a sensor stack 120. The sensor stack can include an electrochemical electrode 130 and a photodetector 140. FIG. 1 further includes sidewalls 112 to graphically illustrate, in part, a location of the microfluidic opening. In some examples, the opening can be an enclosed chamber or an enclosed channel, for example. In this example, the nucleic acid detection device combines an electrochemical sensor and a photodetector to permit the dual sensing detection of an electrochemical signal and an optical signal following nucleic acid amplification. The dual sensing detection allows for simultaneous real time detection, save space on a silicon substrate, and reduces the quantity of silicon used for the dual detection device.

In further detail, the microfluidic opening can be a channel, an open channel, a closed channel, a chamber, a reservoir, or the like. In some examples, the microfluidic opening can be part of a microarray, can be on chip, can be off chip, or the like. The size and shape of the microfluidic opening is not particularly limited. In some examples, however, the microfluidic opening can receive from 1 μL to 10 μL of fluid. In other examples, the microfluidic opening can receive from 10 μL to 10 μL of fluid, or from 50 μL to 200 μL of fluid. The term "fluid" herein refers to liquids, including liquids with solvated compounds and/or dispersed compounds carried by the liquid as a dispersion.

The electrochemical electrode can be formed of a conductive material that can be transparent to a fluorescent emission. As used herein a "fluorescent emission" refers to fluorescence generated when an excitation electromagnetic energy interacts with a fluorescing agent in fluid. The electrochemical electrode can include a first side and an opposite second side. The first side can be exposed to the microfluidic opening. As used herein, "transparent to a fluorescent emission" can indicate an ability to allow a fluorescent emission to pass there through with less than, for example, 20% transmission loss. In other examples, the fluorescent emission can be passed there through with less than 15%, less than 10%, or less than 5% transmission loss.

In some examples, the electrochemical electrode can be absorptive to excitation electromagnetic energy from an external illumination source, such as a light source. As used herein, "excitation electromagnetic energy" can refer to electromagnetic energy, such as in the form of light, emitted from a light source. For example, indium tin oxide (ITO) is absorptive of UV electromagnetic energy at less than about 300 nm. Likewise, dopant can be added to modify the absorption range of a particular material used for the electrochemical electrode. In further detail, a fluorescing agent that may be present in a fluid that the excitation electromagnetic energy passes through can generating a fluorescent emission that can optically pass through the electrochemical electrode to be received by the photodetector. In some example, the attenuation of the excitation electromagnetic energy can be expressed as an absorption ratio of fluorescent emission to light. In one example, the electrochemical electrode can have an absorption ratio of excitation electromagnetic energy (light) to fluorescent emission (light) can be from 10:1 to $10^6$, from 100:1 to $10^5$:1, from $10^3$:1 to $10^6$:1, or from 10:1 to $10^4$:1, for example.

The conductive material can include a conductive metal oxide, a conductive polymer, or a conductive ceramic. The conductive material can be crystalline or amorphous. In one example, the conductive material can include the conductive metal oxide and the conductive metal oxide can be selected from indium tin oxide, tin (IV) oxide, zinc tin oxide, bismuth-doped tin oxide, fluorine-doped tin oxide, or a combination thereof. In another example, the conductive metal oxide can be indium tin oxide. In one other example, the conductive material can be zinc tin oxide. In yet another example, the conductive material can include the conductive polymer and the conductive polymer can include polypyrrole, oxidized derivative of polypyrrole, polythiophene, oxidized derivative of polythiophene, polyaniline, oxidized derivative of polyaniline, polyacetylene, oxidized derivative of polyacetylene, or a combination thereof. In a further example, the conductive material can include the conductive ceramic and can include bismuth strontium calcium copper oxide, yttrium barium copper oxide, thallium barium calcium copper oxide, mercury barium calcium copper oxide, fluorine doped lanthanide iron arsenic oxide, or a combination thereof.

In one example, a thickness of the conductive material can range from 5 nm to 1 μm. In another example, the conductive material can have a thickness that can range from 100 nm to 500 nm, from 250 nm to 750 nm, from 300 nm to 900 nm, from 25 nm to 250 nm, or from 5 nm to 600 nm. In some examples, the thickness of the conductive material can affect the materials ability to be transparent to a fluorescent emissions.

The photodetector can be positioned relative to the second side of the electrochemical electrode to optically receive the fluorescent emission when passed through the electrochemical electrode. The photodetector can detect the fluorescent emission and in one example, can be sized to span the area under the microfluidic opening. In another example, the photodetector can be sized to span one-quarter to three-quarters of the area under the microfluidic opening. In a further example, the photodetector can be sized to span half to three-quarters of the area under the microfluidic opening.

The photodetector can be integrated. In one example, the photodetector can include a pin-photodiode, an avalanche photodiode, a phototransistor, a multi-junction photodiode, a charge coupling device, a complimentary metal-oxide semiconductor, a photo-sensor, a photo-resistor, a pyroelectric detector, a thermopile, or a combination thereof. In one other example, the photodetector can include a pin-photodiode. In another example, the photodetector can include a multi-junction photodiode.

Figure 2:
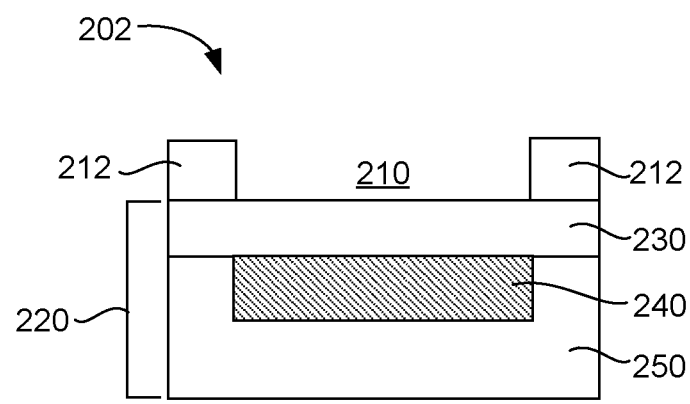
FIG. 2 graphically illustrates an example nucleic acid detection device in accordance with the present disclosure.

Turning now to FIG. 2, in accordance with examples of the present disclosure, a nucleic acid detection device 202 can include a microfluidic opening 210 and a sensor stack 220. The sensor stack can include an electrochemical electrode 230 and a photodetector 240. Sidewalls 112 are also shown which graphically illustrate, in part, a location of the microfluidic opening. In some examples, the nucleic acid detection device can be positioned on a substrate 250.

In further detail, the substrate can include any material when the photodetector is a thin film material. In some examples, the substrate can include a silicon substrate, a silicon germanium substrate, a gallium arsenic substrate, a glass substrate, a plastic, a ceramic, a composite, a metal oxide, a printed circuit board, or a combination thereof. In one example, the substrate can be a silicon substrate.

Figure 3:
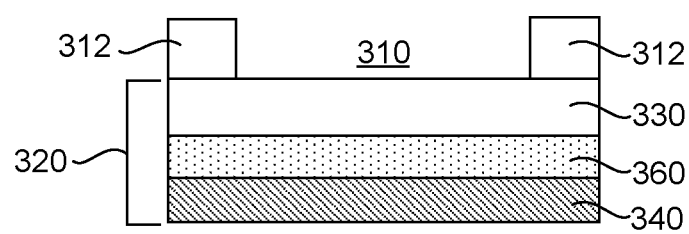
FIG. 3 graphically illustrates an example nucleic acid detection device in accordance with the present disclosure.
Figure 4:
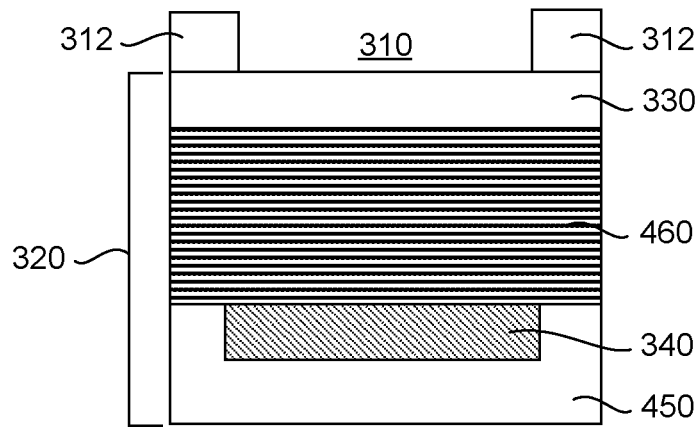
FIG. 4 graphically illustrates an example nucleic acid detection device in accordance with the present disclosure.

Turning now to FIGS. 3 and 4, some of the same structures are shown respectively here that were shown and described in FIGS. 1 and 2, e.g., a nucleic acid detection device 302, 402, respectively, a microfluidic opening 310, and a sensor stack 320. The sensor stack can include an electrochemical electrode 330 and a photodetector 340. Sidewalls 312 are also shown which graphically illustrate, in part, a location of the microfluidic opening. In some examples, the nucleic acid detection device can be positioned on a silicon substrate 450, as shown in FIG. 4, but could also be included in the example of FIG. 3. In these examples, there is also an optically active filter, shown at 360 in FIG. 3 and at 460 in FIG. 4. The optically active filter can be positioned between the conductive material and the photodetector. The optically active filter can be a band pass, notch band, low-pass or high-pass filter. In some examples, the optically active filter can be dye based, dichroic, or fabry-perot etalon.

As shown more specifically in FIG. 3, the optically active filter 360 can be an optically active dye filter. The optically active dye filter can have an average thickness that can vary from 1 μm to 100 μm. In other examples, the optically active dye filter can have an average thickness that can vary from 1 μm to 50 μm, 20 μm to 80 μm, or 10 μm to 40 μm. In some examples, the optically active dye filter can be an absorptive filter.

In another example as shown more specifically in FIG. 4, the optically active filter 460 can be an optically active dichroic filter. The dichroic filter can include alternating refractive material layers, as illustrated schematically by horizontal cross-hatching in FIG. 4. In some examples, the dichroic filter can include from 5 to 250 material layers, from 5 to 25 material layers, from 50 to 200 material layers, from 15 to 150 material layers, from 10 to 15 material layers, or from 8 to 20 material layers. The alternating refractive material layers can be different materials. For example, the material layers can include low refractive index materials, high refractive index materials, and combinations thereof. Examples of low refractive index materials can include aluminum oxide and silicon dioxide. Examples of high refractive index materials can include titanium dioxide, magnesium fluoride, or zinc sulfide. In yet other examples, the material layers can include other material pairs. The individual material layers of a dichroic filter can be less than 1 μm thick. In some examples, the individual material layers can have a thickness that can range from 5 nm to 900 nm, from 5 nm to 400 nm, from 5 nm to 350 nm, from 25 nm to 250 nm, from 50 nm to 500 nm, or from 300 nm to 900 nm. A thickness of the entire dichroic filter can range from 0.5 μm to 100 μm, from 1 μm to 10 μm, from 5 μm to 75 μm, or from 0.5 μm to 25 μm.

Regardless of the configuration of the nucleic acid detection device, in some examples, a nucleic acid detection device can be integrated on a microfluidic chip, such as a lab-on-a-chip device. In one example, the microfluidic chip can be an integrated point of care diagnostic device, such as an in vitro diagnostic point of care device.

Figure 5:
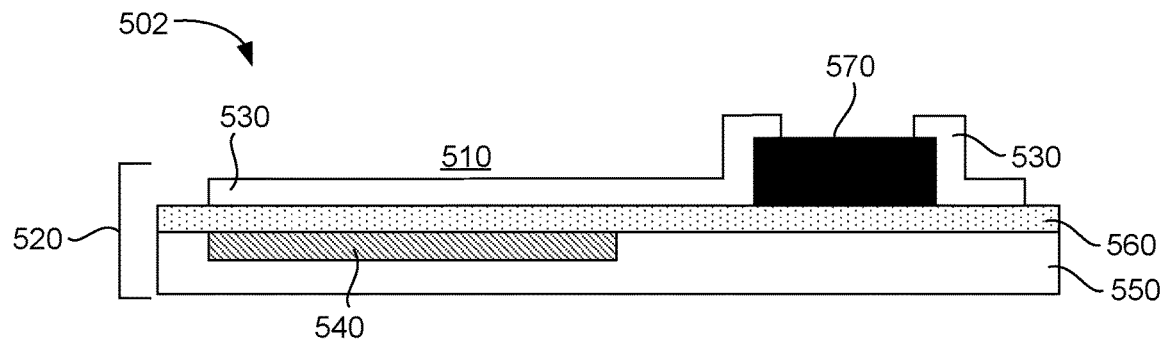
FIG. 5 graphically illustrates an example nucleic acid detection device in accordance with the present disclosure.
Figure 6:
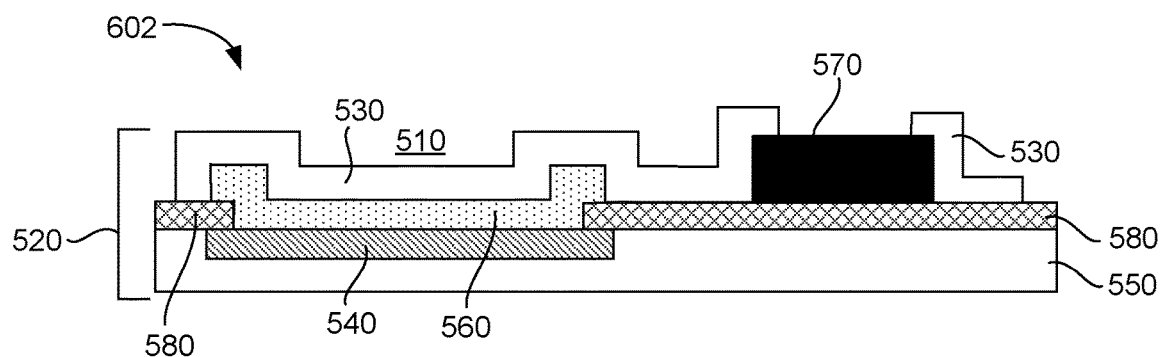
FIG. 6 graphically illustrates an example nucleic acid detection device in accordance with the present disclosure.
Figure 7:
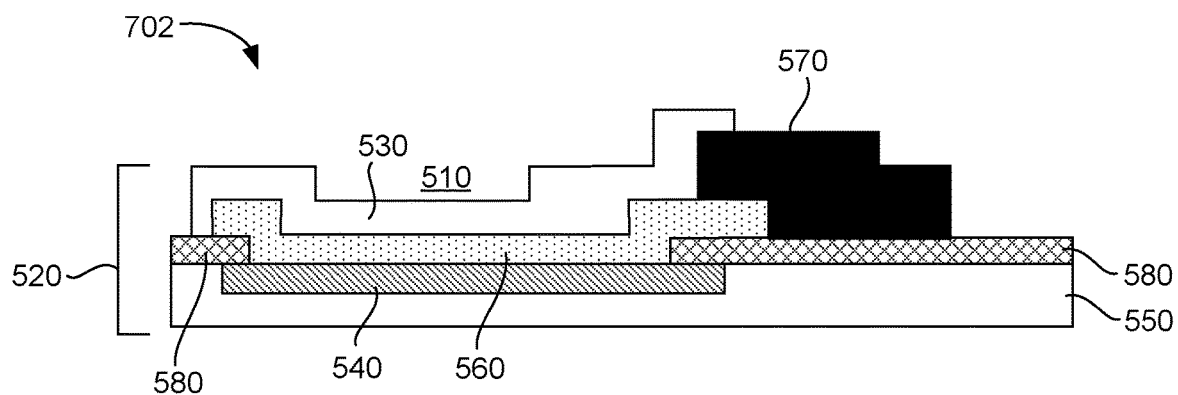
FIG. 7 graphically illustrates an example nucleic acid detection device in accordance with the present disclosure.

Turning now to FIG. 5, an example of a nucleic acid detection device is shown at 502. Likewise, in FIG. 6 and FIG. 7, alternative nucleic acid detection devices are shown at 602, and 702 respectively. These devices can be part of an integrated sensor design, for example. Some of the same type of structures are shown respectively here that were shown and described in FIGS. 1-4, e.g., a microfluidic opening 510, a sensor stack 520 that can include an electrochemical electrode 530 and a photodetector 540. In some examples, the nucleic acid detection device can be positioned on a silicon substrate 550. The integrated sensor design can further include, as shown in these examples, a reference electrode 570. In some examples, as shown in FIG. 6 and FIG. 7, there can also be an insulative layer 580, e.g., $Si_3N_4$/SiC (DSO) insulative layer.

Figure 8A:
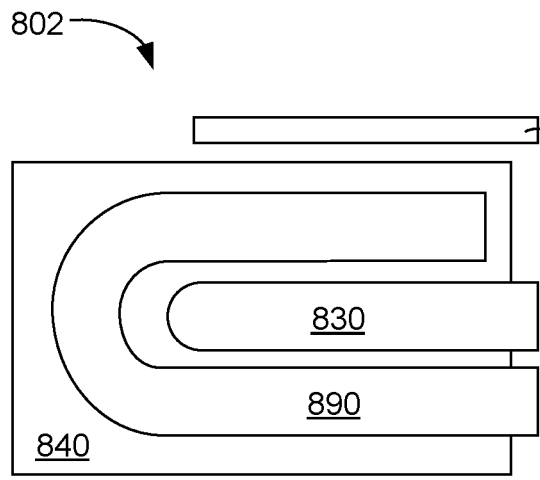
FIG. 8A graphically illustrates a top view of an example multiplex nucleic acid detection device in accordance with the present disclosure.
Figure 8B:
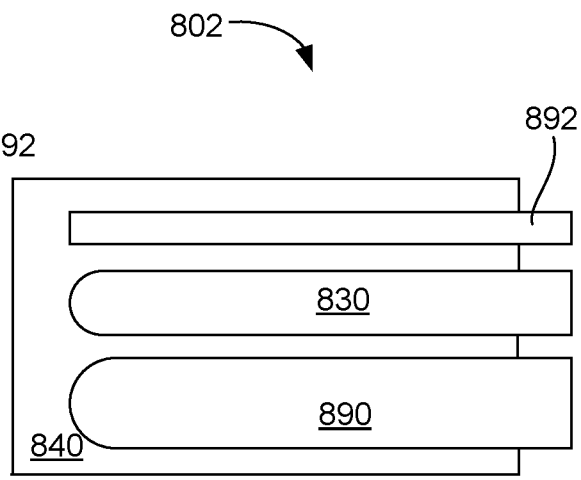
FIG. 8B graphically illustrates a top view of an example multiplex nucleic acid detection device in accordance with the present disclosure.

In some examples, an integrated sensor design can have a design as shown in a partial top view in FIG. 8A and in partial side view in FIG. 8B. For example, the integrated sensor design can be part of a lab on chip device and can include a reference electrode 892 and a counter electrode 890. The integrated sensor design can be arranged in an array. Other structures previously described can also be present, including an electrochemical electrode 830 and a photodetector 840 as part of a sensor stack.

With respect to the electrodes, the reference electrode can allow for the measurement of an electrochemical response generated at an electrochemical electrode. The reference electrode can be constructed to have a stable and known electrode potential, and can be used in a half-cell, or in some other cell configuration, to provide a reference for evaluating a material based on its electrochemical signature. In one example, the reference electrode can have stable electrical properties. The range of the electrical potential for the reference cell can be from −500 mV to 500 mV compared to a standard hydrogen electrode, which is defined as having 0 V. A counter-electrode can close an electric circuit and balance a reaction occurring at the working electrochemical electrode. In one example, a counter-electrode can act electrically with respect to the working electrochemical electrode to thereby provide a circuit over which a current can be measured and evaluated for an electrical signature with respect to the reference electrode. In some examples, the counter-electrode can be a common counter-electrode (a shared counter electrode) for multiple electrochemical electrodes.

Figure 9:
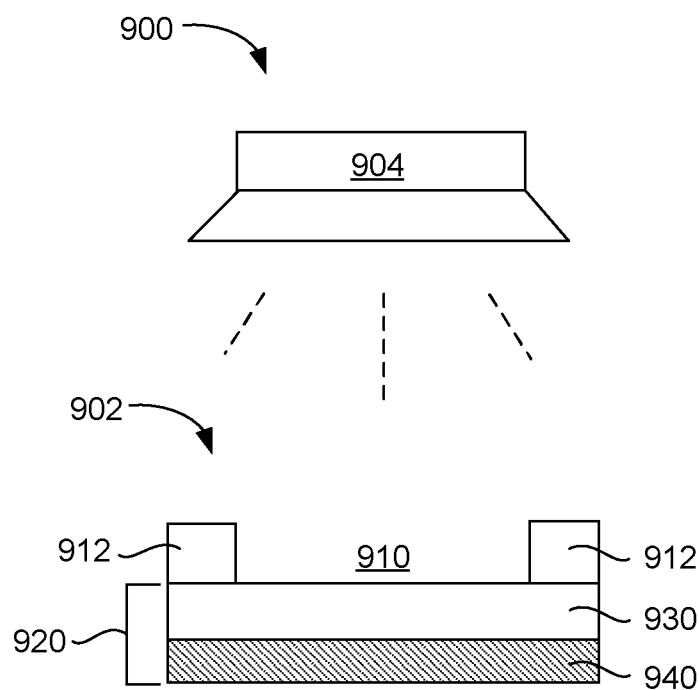
FIG. 9 graphically illustrates an example nucleic acid detection system in accordance with the present disclosure.

In another example, a multiplex nucleic acid detection system 900 is shown in FIG. 9. The system can include a nucleic acid detection device 902 and a light source 904. The nucleic acid detection device can include a microfluidic opening 910 and a sensor stack 920. The sensor stack can include an electrochemical electrode 930 and a photodetector 940. FIG. 9 further includes sidewalls 912 to graphically illustrate, in part, a location of the microfluidic opening. In one example, the light source can emit an excitation electromagnetic energy. The excitation electromagnetic energy can be operable to interact with a fluorescing agent in a fluid and generate a fluorescence emission that can pass through the electrochemical electrode to be received by the photodetector. In some examples, the light source can include a blue LED with a short path filter with cut of wavelength 490 nm. In another example, the fluorescent emission can have a wavelength ranging from 360 nm to 800 nm and the conductive material can be transparent to the frequency. In other examples, the fluorescent emission can have a frequency ranging from 505 nm to 800 nm, from 505 nm to 650 nm, from 560 nm to 680 nm, from 625 nm to 680 nm, or from 680 nm to 780 nm. In another example, the system can further include a nucleic acid amplifying solution. The nucleic acid amplifying solution can include a polymerase, a nucleotide mix, magnesium salt, a nucleic acid oligomer, a redox-active intercalating dye, a fluorescent intercalating dye or other type of probes and other secondary reagents.

Figure 10:
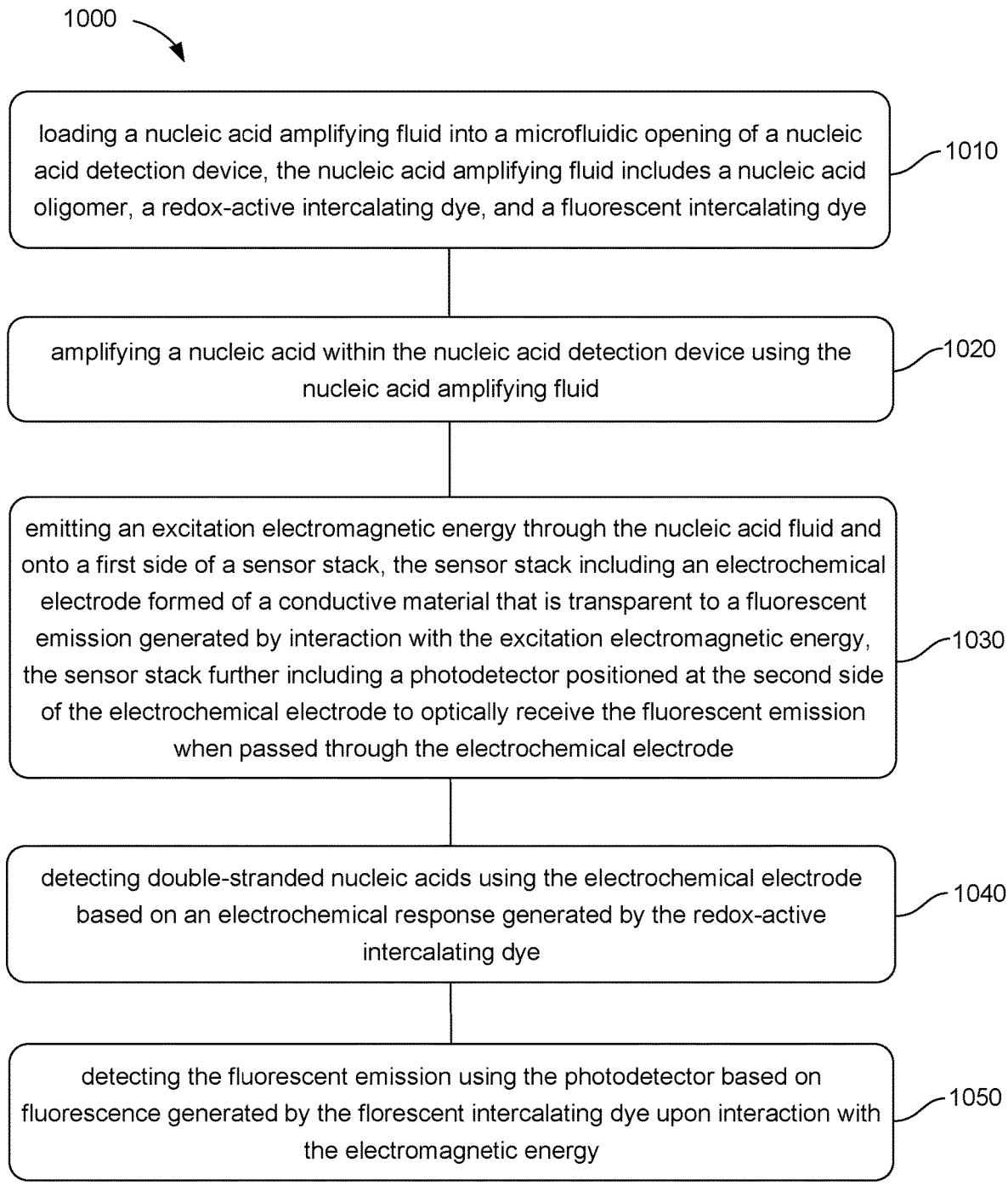
FIG. 10 is a flow diagram illustrating an example method of nucleic acid amplification detection in accordance with the present disclosure.

A flow diagram of an example method of nucleic acid detection 1000 is shown in FIG. 10. The method can include loading 1010 a nucleic acid amplifying fluid into a microfluidic opening of a nucleic acid detection device, wherein the nucleic acid amplifying fluid includes a nucleic acid oligomer, a redox-active intercalating dye, and a fluorescent intercalating dye. The method also include amplifying 1020 a nucleic acid within the nucleic acid detection device using the nucleic acid amplifying fluid, and emitting 1030 an excitation electromagnetic energy through the nucleic acid fluid and onto a first side of a sensor stack. The sensor stack includes an electrochemical electrode formed of a conductive material that is transparent to a fluorescent emission generated by interaction with the excitation electromagnetic energy. The sensor stack further including a photodetector positioned at the second side of the electrochemical electrode to optically receive the fluorescent emission when passed through the electrochemical electrode. The method also includes detecting 1040 double-stranded nucleic acids using the electrochemical electrode based on an electrochemical response generated by the redox-active intercalating dye, and detecting 1050 the fluorescent emission using the photodetector based on fluorescence generated by the florescent intercalating dye upon interaction with the electromagnetic energy. In one example, the method can further include simultaneously measuring a real time strength of an electrochemical response generated during amplification by the redox-active intercalating dye and fluorescent emissions generated during amplification by the fluorescent intercalating dye.

In further detail, loading the nucleic acid amplifying solution can include injecting from 10 μL to 10 μL of a nucleic acid amplifying solution into the microfluidic opening of the nucleic acid amplification device. In some examples, injecting can include pipetting, fluid ejecting, or the like. Amplifying a nucleic acid within the electrochemical cell can include polymerase chain reaction (PCR), strand displacement assay, transcription mediated assay, isothermal amplification, loop mediated isothermal amplification, reverse-transcription loop mediated isothermal amplification, nucleic acid sequence based amplification, recombinase polymerase amplification, or multiple displacement amplification. In one example, amplification can include polymerase chain reaction, such as reverse transcription polymerase chain reaction. During amplification, hydrogen bonds on a double-stranded nucleic acid can be denatured and two single strands of nucleic acid can be produced.

Detection of the nucleic acid amplification can include measuring an electrical signal generated by the redox-active intercalating dye. In one example, the signal can be measured by the electrochemical electrode. In some examples, the method can further include analyzing the electrical signal detected by comparing it to a reference signal measured at a reference electrode.

Detection of the nucleic acid amplification can also include detecting a fluorescent emission based on the fluorescence of the florescent intercalating dye. The fluorescence emission can be detected by the photodetector.

In some examples, the method can further include simultaneously measuring a real time strength of an electrochemical response generated during amplification by the redox-active intercalating dye and fluorescent emissions generated during amplification by the fluorescent intercalating dye. The measuring can include detecting a signal continuously or detecting a signal at set intervals. For example, the measuring can include detecting a signal at intervals such as a time within the range of every 1 second to every 10 seconds, every 5 seconds to every 60 seconds, every one minute to every five minutes, or some other suitable time frame based on the measurements to be taken.

In yet another example, the method can further include thermal cycling the nucleic acid amplifying fluid within the electrochemical cell for in situ nucleic acid amplification. Thermal cycling can include denaturing, annealing, and extending nucleic acid chains based on temperature changes. A "thermal cycle" can be defined by the temperatures used for denaturing, annealing, and extending phases of the amplification. An increased temperature can cause hydrogen bonds between bases in a double-stranded nucleic acid sample to break apart resulting in two single strands or nucleic acid realized from a formerly double stranded nucleic acid. During annealing, the heated sample can then be cooled, enabling single stranded nucleic acid oligomers, such as primers, to attach to the complimentary nitrogen bases on the single strands of the nucleic acid. During extending of the nucleic acid chain the temperature may be increased, for example, to enable a polymerase enzyme to extend the nucleic acid strand by adding nucleic acid bases. Regardless of the sequence or heating and cooling and the temperatures that are reached during the heating and cooling phases, thermal cycling can be repeated until a desired number of nucleic acid copies, e.g., DNA, are formed, which can for example take from about 10 to about 50 thermal cycles, or 20 to 45 thermal cycles, or 10 to 30 thermal cycles, in many instances.

In some examples, temperature changes can be controlled by an internal heating element of a microfluidic chip. In other examples, temperature changes can be controlled by an external heating element. In yet other examples, the method can include cooling utilizing an internal cooling element or an external cooling device.

As used in this specification and the appended claims, the singular forms "a," "an," and "the" include plural referents unless the content clearly dictates otherwise.

As used herein, a plurality of items, structural elements, compositional elements, and/or materials may be presented in a common list for convenience. However, these lists should be construed as though the individual member of the list is identified as a separate and unique member. Thus, no individual member of such list should be construed as a de facto equivalent of any other member of the same list based on their presentation in a common group without indications to the contrary.

Concentrations, dimensions, amounts, and other numerical data may be presented herein in a range format. A range format is used merely for convenience and brevity and should be interpreted flexibly to include the numerical values explicitly recited as the limits of the range, as well as to include all the individual numerical values or sub-ranges encompassed within that range as the individual numerical value and/or sub-range is explicitly recited. For example, a wavelength range from about 350 nm to about 800 nm should be interpreted to include the explicitly recited limits of 350 nm and 800 nm and to include individual wavelengths such as about 400 nm, 500 nm, and 600 nm, and sub-ranges such as about 350 nm to 500 nm, about 450 nm to 750 nm, from about 400 nm to 600 nm, etc.

The following illustrates an example of the present disclosure. However, it is to be understood that the following is illustrative of the application of the principles of the present disclosure as presented herein. Numerous modifications and alternative devices, compositions, methods, systems, etc., may be devised without departing from the present disclosure.

Example—Excitation Electromagnetic Energy Transmittance and Absorption Through Indium Tin Oxide (ITO) and Optical Detection Therethrough Transmittance of light was measured by an optical detection device and a nucleic acid detection device in order to determine the effect of an electrochemical electrode on transmittance. The optical detection device and the nucleic acid detection device were structurally similar.

The optical detection device included a microfluidic opening, an 888.43 nm thick optically active dichroic filter, a silicon photo diode, and a silicon substrate. The optically active dichroic filter included 16 alternating silicon dioxide and tin dioxide layers as shown in Table 1.

TABLE 1

| Optically Active Dichroic Filter | |
|---|---|
| Layer | Thickness (nm) |
| $SiO_2$ | 39.76 |
| $TiO_2$ | 40.60 |
| $SiO_2$ | 82.82 |
| $TiO_2$ | 51.19 |
| $SiO_2$ | 68.75 |
| $TiO_2$ | 38.14 |
| $SiO_2$ | 71.35 |
| $TiO_2$ | 50.79 |
| $SiO_2$ | 79.30 |
| $TiO_2$ | 42.67 |
| $SiO_2$ | 58.78 |
| $TiO_2$ | 47.37 |
| $SiO_2$ | 83.91 |

TABLE 1-continued

| Optically Active Dichroic Filter | |
|---|---|
| Layer | Thickness (nm) |
| $TiO_2$ | 51.87 |
| $SiO_2$ | 33.17 |
| $TiO_2$ | 47.96 |
| Total | 888.43 |

The nucleic acid detection device included the components of the optical detection device and a 20 nm thick indium tin oxide electrochemical electrode over the optically active dichroic filter.

Figure 11:
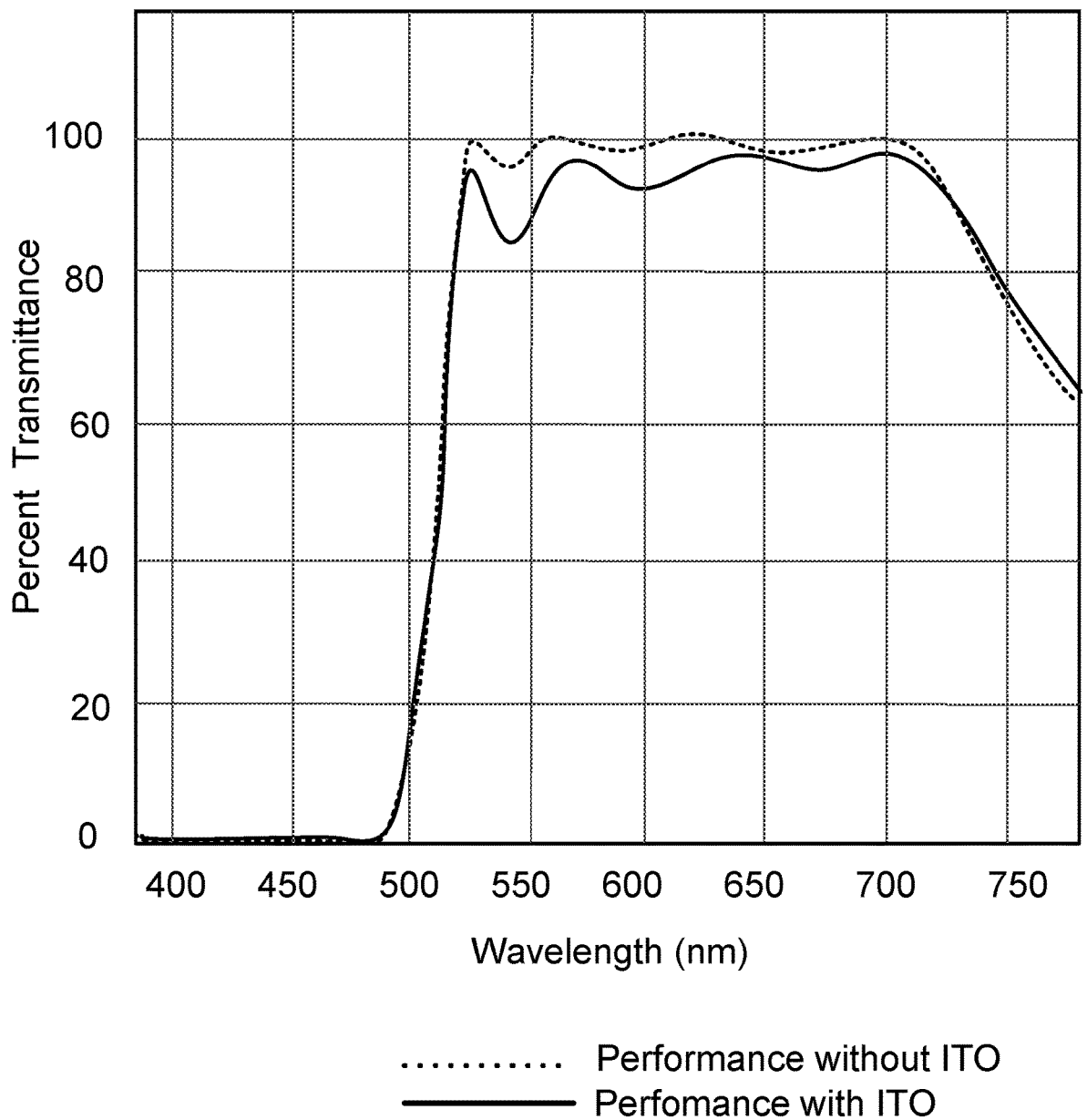
FIG. 11 graphically illustrates optical detector readings of a fluorescence signal generated from a nucleic acid detection device in accordance with an example of the present disclosure.

In order to test the effect of the indium tin oxide electrochemical electrode on transmittance a light source was emitted at both of the devices. The spectral response was evaluated in a wavelength ranging from 400 nm to 800 nm and the percent transmittance was measured by a spectrophotometer. The results of the optical detection are graphically presented in FIG. 11 as percent transmittance vs. wavelength. The results illustrate that combining an indium tin oxide electrochemical electrode with an optical detector has a minimal impact on transmittance.

It was further found that when an indium tin oxide electrochemical electrode was excluded that transmission of fluorescence was slightly better; however there was poor rejection of excitation electromagnetic energy. It was also found that when an indium tin oxide electrochemical electrode was included that transmission of fluorescence was slightly worse; however there was better rejection (absorption) of excitation electromagnetic energy. Thus, even though slightly worse fluorescence transmission occurs with the presence of the electrochemical electrode, it still passed through for an optical measurement, with the added benefit of providing an electrochemical electrode being present for an electrochemical measurement to be available along with the fluorescent optical measurement.

While the present technology has been described with reference to certain examples, various modifications, changes, omissions, and substitutions can be made without departing from the disclosure.

What is claimed is:

1. A dual-sensing nucleic acid detection device that combines an electrochemical sensor and an integrated photodetector for simultaneous detection of an electrical signal and an optical signal, respectively, the nucleic acid detection device comprising:
a microfluidic opening in a channel or a chamber, wherein the channel or chamber is configured to receive from 1 μL to 10 μL of a fluid;
and
a sensor stack embedded in or disposed on a substrate, the sensor stack comprising:
an electrochemical electrode formed of a conductive material that is transparent to a fluorescent emission, the electrochemical electrode including a first side and a second side oriented opposite of the first side, wherein the first side is exposed to the channel or chamber;
a counter electrode to provide a circuit over which a current can be measured with respect to a reference electrode; and
the integrated photodetector coupled to the second side of the electrochemical electrode and to the counter electrode, the integrated photodetector configured to optically receive the fluorescent emission when passed through the electrochemical electrode.

2. The nucleic acid detection device of claim 1, wherein the conductive material comprises a conductive metal oxide, a conductive polymer, or a conductive ceramic.

3. The nucleic acid detection device of claim 2, wherein the conductive material comprises the conductive metal oxide and is selected from indium tin oxide, tin (IV) oxide, zinc tin oxide, bismuth-doped tin oxide, fluorine-doped tin oxide, or a combination thereof.

4. The nucleic acid detection device of claim 2, wherein the conductive material comprises the conductive polymer and is selected from polypyrrole, oxidized derivative of polypyrrole, polythiophene, oxidized derivative of polythiophene, polyaniline, oxidized derivative of polyaniline, polyacetylene, oxidized derivative of polyacetylene, or a combination thereof.

5. The nucleic acid detection device of claim 2, wherein the conductive material comprises the conductive ceramic and is selected from bismuth strontium calcium copper oxide, yttrium barium copper oxide, thallium barium calcium copper oxide, mercury barium calcium copper oxide, fluorine doped lanthanide iron arsenic oxide, or a combination thereof.

6. The nucleic acid detection device of claim 1, wherein the integrated photodetector comprises a pin-photodiode, an avalanche photodiode, a phototransistor, a multi junction photodiode, a charge coupling device, a complimentary metal-oxide semiconductor, a photo-sensor, a photo-resistor, a pyroelectric detector, a thermopile, or a combination thereof.

7. The nucleic acid detection device of claim 1, further comprising an optically active dye filter having an average thickness from 1 μm to 100 μm located between the electrochemical electrode and the integrated photodetector.

8. The nucleic acid detection device of claim 1, further comprising an optically active dichroic filter having an average thickness from 0.5 μm to 100 μm located between the electrochemical electrode and the integrated photodetector.

9. The nucleic acid detection device of claim 8, wherein the optically active dichroic filter includes from 5 to 250 individual layers, the individual layers having an average thickness ranging from 5 nm to 400 nm.

10. A multiplex nucleic acid detection system, comprising:
a nucleic acid detection device that combines an electrochemical sensor and an integrated photodetector for simultaneous detection of an electrical signal and an optical signal, respectively, the nucleic acid detection device including:
a microfluidic opening in a channel or a chamber, wherein the channel or chamber is configured to receive from 1 μL to 10 μL of a fluid, and
a sensor stack embedded in or disposed on a substrate, including:
an electrochemical electrode formed of a conductive material that is transparent to a fluorescent emission, the electrochemical electrode including a first side and a second side oriented opposite of the first side, wherein the first side is exposed to the microfluidic opening,
a reference electrode;
a counter electrode to provide a circuit over which a current can be measured with respect to the reference electrode; and
the integrated photodetector coupled to the second side of the electrochemical electrode, to the reference electrode, and to the counter electrode, the integrated photodetector configured to optically receive the fluorescent emission when passed through the electrochemical electrode; and
a light source to emit excitation electromagnetic energy onto the first side of the electrochemical electrode through the microfluidic opening.

11. The multiplex nucleic acid detection system of claim 10, further comprising a fluid including a fluorescing agent to interact with the excitation electromagnetic energy and emit a fluorescent emission, wherein the conductive material absorbs the excitation electromagnetic energy and is transparent to the fluorescent emission.

12. The multiplex nucleic acid detection system of claim 11, wherein the fluid is a nucleic acid amplifying solution including a nucleic acid oligomer, a redox-active intercalating dye, or a combination thereof, and wherein the fluorescing agent includes and a fluorescent intercalating dye.

13. A method of nucleic acid detection with simultaneous detection of an electrical signal using an electrochemical sensor an optical signal using an integrated photodetector, comprising:
loading a nucleic acid amplifying fluid into a microfluidic opening of a nucleic acid detection device, the nucleic acid amplifying fluid includes a nucleic acid oligomer, a redox-active intercalating dye, and a fluorescent intercalating dye, the microfluidic opening being located within a channel or a chamber structurally configured to receive from 1 μL to 10 μL of the nucleic acid amplifying fluid;
amplifying a nucleic acid within the nucleic acid detection device using the nucleic acid amplifying fluid;
emitting an excitation electromagnetic energy through the nucleic acid amplifying fluid and onto a first side of a sensor stack embedded in or disposed on a substrate, the sensor stack including:
an electrochemical electrode having a first side and a second side positioned opposite of the first side, the electrochemical electrode formed of a conductive material that is transparent to a fluorescent emission generated by interaction with the excitation electromagnetic energy,
the integrated photodetector coupled to the second side of the electrochemical electrode, the integrated photodetector configured to optically receive the fluorescent emission when passed through the electrochemical electrode;
detecting double-stranded nucleic acids using the electrochemical electrode based on an electrochemical response generated by the redox-active intercalating dye, comprising measuring a current with respect to a reference electrode; and
detecting the fluorescent emission using the integrated photodetector based on fluorescence generated by the fluorescent intercalating dye upon interaction with the excitation electromagnetic energy.

14. The method of nucleic acid detection of claim 13, further comprising simultaneously measuring a real time strength of the electrochemical response generated during amplification by the redox-active intercalating dye and the fluorescent emission generated during amplification by the fluorescent intercalating dye.

15. The nucleic acid detection device of claim 1, wherein the counter electrode is a shared counter electrode of a second electrochemical electrode.

16. The nucleic acid detection device of claim 1, further comprising an optically active filter positioned between the conductive material and the integrated photodetector, the optically active filter comprising five or more alternating refractive material layers.

17. The nucleic acid detection device of claim 16, wherein the alternating refractive material layers comprise different materials with varying refractive indices.

18. The nucleic acid detection device of claim 1, wherein the reference electrode has an electric potential from −500 mV to 500 mV compared to a standard hydrogen electrode.

* * * * *